United States Patent
Shibasaki et al.

(10) Patent No.: US 10,413,892 B2
(45) Date of Patent: Sep. 17, 2019

(54) CATALYST, PRODUCTION METHOD THEREFOR, AND METHOD FOR PRODUCING OPTICALLY ACTIVE ANTI-1, 2-NITROALKANOL COMPOUND

(71) Applicant: Microbial Chemistry Research Foundation, Shinagawa-ku, Tokyo (JP)

(72) Inventors: Masakatsu Shibasaki, Tokyo (JP); Naoya Kumagai, Tokyo (JP); Akihito Nonoyama, Tokyo (JP); Kazuki Hashimoto, Tokyo (JP); Akira Saito, Tokyo (JP)

(73) Assignee: Microbial Chemistry Research Foundation, Shinagawa-ku, Tokyo (JP)

( * ) Notice: Subject to any disclaimer, the term of this patent is extended or adjusted under 35 U.S.C. 154(b) by 0 days.

(21) Appl. No.: 15/778,376

(22) PCT Filed: Nov. 21, 2016

(86) PCT No.: PCT/JP2016/084515
§ 371 (c)(1),
(2) Date: May 23, 2018

(87) PCT Pub. No.: WO2017/090569
PCT Pub. Date: Jun. 1, 2017

(65) Prior Publication Data
US 2018/0345260 A1 Dec. 6, 2018

(30) Foreign Application Priority Data

Nov. 24, 2015 (JP) ................................. 2015-229127

(51) Int. Cl.
| | | |
|---|---|---|
| *B01J 31/00* | (2006.01) | |
| *C07C 201/00* | (2006.01) | |
| *C07C 205/00* | (2006.01) | |
| *C07C 237/00* | (2006.01) | |
| *B01J 31/22* | (2006.01) | |
| *B01J 37/04* | (2006.01) | |
| *C07C 201/12* | (2006.01) | |
| *C07C 205/16* | (2006.01) | |
| *C07C 205/32* | (2006.01) | |
| *C07C 205/54* | (2006.01) | |
| *C07C 237/04* | (2006.01) | |
| *C07B 61/00* | (2006.01) | |

(52) U.S. Cl.
CPC .............. *B01J 31/22* (2013.01); *B01J 37/04* (2013.01); *C07C 201/12* (2013.01); *C07C 205/16* (2013.01); *C07C 205/32* (2013.01); *C07C 205/54* (2013.01); *C07C 237/04* (2013.01); *B01J 2231/341* (2013.01); *B01J 2531/004* (2013.01); *B01J 2531/12* (2013.01); *B01J 2531/38* (2013.01); *C07B 61/00* (2013.01)

(58) Field of Classification Search
CPC ....... B01J 31/22; C07C 201/12; C07C 205/16; C07C 205/54; C07C 237/04
See application file for complete search history.

(56) References Cited

U.S. PATENT DOCUMENTS

2015/0375219 A1    12/2015  Shibasaki et al.

FOREIGN PATENT DOCUMENTS

| CN | 105073257 | 11/2015 |
|---|---|---|
| JP | 61-238764 | 10/1986 |
| JP | 2009-114071 | 5/2009 |
| JP | 2010-189374 | 9/2010 |
| JP | 2014-151313 | 8/2014 |
| WO | 2010084772 | 7/2010 |
| WO | 2014126008 | 8/2014 |
| WO | 2015166827 | 11/2015 |

OTHER PUBLICATIONS

Sureshkumar et al. A Modified Preparation Procedure for Carbon Nanotube-Confined Nd/Na Heterobimetallic Catalyst for anti-Selective Catalytic Asymmetric Nitroaldol Reactions. Journal of Organic Chemistry, vol. 78, 11494-11500. (Year: 2013).*
Nitabaru et al. anti-Selective Catalytic Asymmetric Nitroaldol Reaction via a Heterobimetallic Heterogeneous Catalyst. Journal of the American Chemical Society, vol. 131, 13860-13869. (Year: 2009).*
Smith, et al., "Biphenyl-Substituted Oxazolidinones as Cholesteryl Ester Transfer Protein Inhibitors: Modifications of the Oxazolidinone Ring Leading to the Discovery of Anacetrapib," Journal of Medicinal Chemistry, vol. 54, pp. 1880-4895, Jun. 17, 2011.
Uraguchi, et al., "Chiral Tetraaminophosphonium Salt-Mediated Asymmetric Direct Henry Reaction," J. Am. Chem. Soc., vol. 129, No. 41, pp. 12392-12393, Jul. 11, 2007.
Taiwan Intellectual Property Office, Taiwanese First Office Action issued in corresponding Taiwanese Application No. 105138423, dated Jun. 12, 2017.
Ogawa, et al., "Self-Assembling Neodymium/Sodium Heterobimetallic Asymmetric Catalyst Confined in a Carbon anotube Network," Angewandte Communications Int. Ed., vol. 52, No. 24, pp. 6196-6201, Jun. 10, 2013.

* cited by examiner

*Primary Examiner* — Sikarl A Witherspoon
(74) *Attorney, Agent, or Firm* — Carmody Torrance Sandak & Hennessey LLP

(57) ABSTRACT

A catalyst including: neodymium; sodium; and a ligand, which is a compound expressed by Structural Formula (1) below, wherein the neodymium and the ligand form a complex at a molar ratio of 1:2 (neodymium:ligand):

Structural Formula (1)

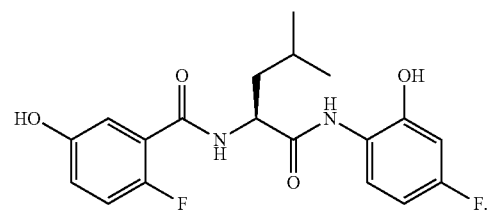

10 Claims, 1 Drawing Sheet

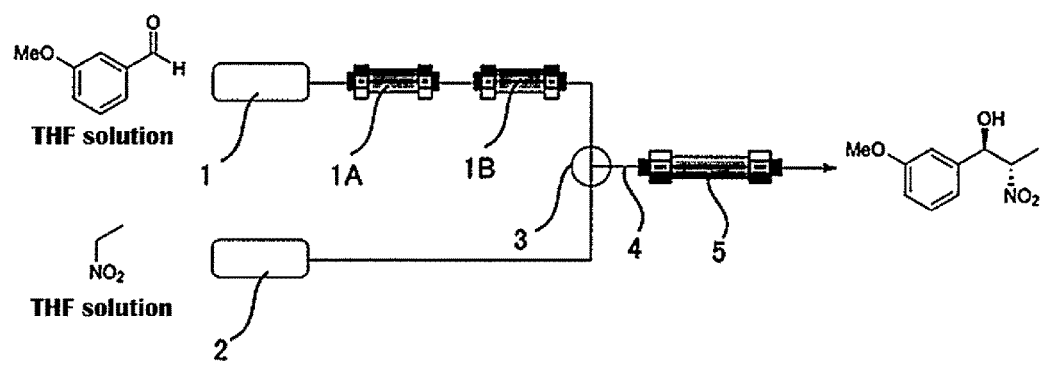

CATALYST, PRODUCTION METHOD THEREFOR, AND METHOD FOR PRODUCING OPTICALLY ACTIVE ANTI-1,2-NITROALKANOL COMPOUND

TECHNICAL FIELD

The present invention relates to a catalyst useful in anti-selective catalytic asymmetric nitroaldol reaction, a method for producing the same, and a method for producing an optically active anti-1,2-nitroalkanol compound using the catalyst.

BACKGROUND ART

Optically active anti-1,2-nitroalkanol compounds are useful as precursors of optically active anti-1,2-aminoalcohol compounds.

Optically active anti-1,2-aminoalcohol compounds are generally used as chiral building blocks having very high utility in organic synthetic chemistry, especially medicinal synthetic chemistry. For example, the optically active anti-1,2-aminoalcohol compounds are contained as basic units in pharmaceutical products such as β-agonist, many naturally-occurring biologically active compounds, and the like. Use of optically active anti-1,2-aminoalcohol compounds as starting materials or reaction reagents makes it possible to efficiently and inexpensively produce compounds that can be used for the synthesis of various pharmaceuticals or naturally-occurring biologically active compounds.

Also, the optically active anti-1,2-nitroalkanol compounds themselves are useful as starting materials of pharmaceutical products.

For example, a compound expressed by the following structural formula (anacetrapib), which is regarded to be promising as an inhibitory drug for CETP (cholesteryl ester transfer protein), can be synthesized from optically active anti-1,2-nitroalkanol compounds (see, for example, NPL 1). Note that, in this proposed technique, a racemate of optically active anti-1,2-nitroalkanol compounds is used to obtain anacetrapib through optical resolution.

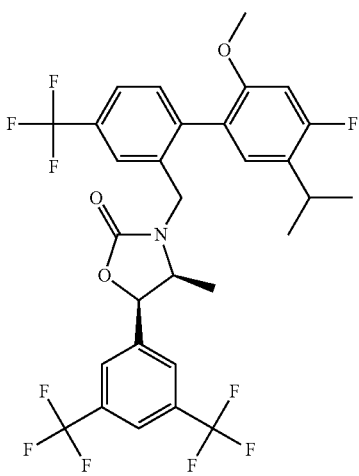 [SMILES: COc1cc(F)c(C(C)C)cc1-c1ccc(C(F)(F)F)cc1CN1C(=O)O[C@H](c2cc(C(F)(F)F)cc(C(F)(F)F)c2)[C@@H]1C]

One known method for anti-selectively producing the optically active anti-1,2-nitroalkanol compounds through catalytic asymmetric reaction is a method of allowing various aldehyde compounds and nitroalkane compounds to react in the presence of optically active tetraaminophosphonium salts (see, for example, NPL 2).

This method, however, has to be performed at an extremely low temperature of −78° C. and has a problem that it cannot be applied as an industrial production method.

In view of this, the present inventors proposed a method for anti-selectively producing optically active anti-1,2-nitroalkanol compounds through catalytic asymmetric reaction and a catalyst used in this reaction (see PTL 1).

In this proposed technique, nitroaldol reaction using various aldehyde compounds and nitroalkane compounds is performed using as a catalyst a heterogeneous composite metallic complex, in which a ligand of a specific amide compound is coordinated with lanthanoid such as neodymium and an alkali metal such as sodium. Use of it attains synthesis of optically active anti-1,2-nitroalkanol compounds with high anti-selectivity and very high enantiomeric excess. Also, the nitroaldol reaction rapidly proceeds even under cooling at about −40° C.

Further, as a catalyst that is useful in anti-selective catalytic asymmetric nitroaldol reaction and is reusable, the present inventors proposed a catalyst obtained by mixing a specific amide compound, a nitroalkane compound, a neodymium-containing compound, a sodium-containing compound, and a carbon structure (see PTL 2).

However, the neodymium-containing compound [Nd(O$^i$Pr)$_3$] and the sodium-containing compound [sodium bis(trimethylsilyl)amide (NaHMDS)], serving as starting materials of the catalyst, specifically used in these proposed techniques of the present inventors, are substances that are instable to the atmosphere and thus are necessary to handle in a glove box. In particular, NdO$_{1/5}$(O$^i$Pr)$_{13/5}$ and Nd(O$^i$Pr)$_3$ are very expensive.

Accordingly, at present, there is a demand to provide a catalyst that can be stably prepared and is inexpensive from the viewpoints of enhancing practical usability of anti-selective catalytic asymmetric nitroaldol reaction.

CITATION LIST

Patent Literature

PTL 1: Japanese Patent Application Laid-Open (JP-A) No. 2010-189374
PTL 2: JP-A No. 2014-151313

Non-Patent Literature

NPL 1: Cameron J. Smith, et al., J. Med. Chem., 2011, 54, 4880-4895
NPL 2: Uraguchi, D., et al., J. Am. Chem. Soc., 129, pp. 12392, 2007

SUMMARY OF INVENTION

Technical Problem

The present invention aims to solve the above existing problems and achieve the following object. That is, an object of the present invention is to provide a catalyst that is capable of synthesizing an optically active anti-1,2-nitroalkanol compound with high anti-selectivity and very high enatiomeric excess and further can be stably prepared and is inexpensive; to provide a stable and inexpenive method for producing the catalyst; and a method for producing an optically active anti-1,2-nitroalkanol compound using the catalyst.

Solution to Problem

Means for solving the above problem are as follows.

A catalyst of the present invention is a catalyst including neodymium, sodium, and a ligand that is a compound expressed by Structural Formula (1) below, wherein the neodymium and the ligand form a complex at a molar ratio of 1:2 (neodymium:ligand).

Structural Formula (1)

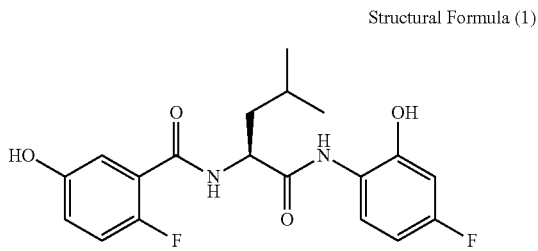 [SMILES: CC(C)C[C@H](NC(=O)c1cc(O)ccc1F)C(=O)Nc1ccc(F)cc1O]

A method of the present invention for producing an optically active anti-1,2-nitroalkanol compound includes allowing an aldehyde compound and a nitroalkane compound having 2 or more carbon atoms to react in the presence of the above catalyst.

A method of the present invention for producing a catalyst includes mixing a compound expressed by Structural Formula (1) below, neodymium halide, and sodium alkoxide.

Structural Formula (1)

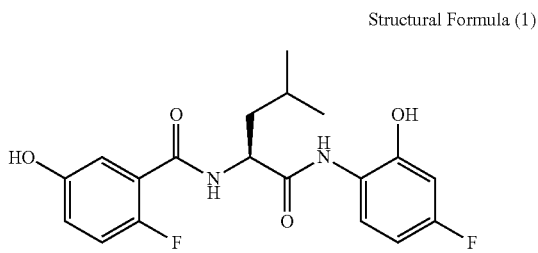 [SMILES: CC(C)C[C@H](NC(=O)c1cc(O)ccc1F)C(=O)Nc1ccc(F)cc1O]

Advantageous Effects of Invention

The present invention can solve the above existing problems and achieve the above object, and can provide a catalyst that is capable of synthesizing an optically active anti-1,2-nitroalkanol compound with high anti-selectivity and very high enatiomeric excess and further can be stably prepared and is inexpensive. Also, the present invention can provide a stable and inexpenive method for producing the catalyst. Also, the present invention can provide a method for producing an optically active anti-1,2-nitroalkanol compound using the catalyst.

BRIEF DESCRIPTION OF DRAWINGS

FIG. 1 is a schematic view for explaining continuous production of an optically active anti-1,2-nitroalkanol compound.

DESCRIPTION OF EMBODIMENTS

Steric configurations in the chemical formulas and the general formulas described in the present specification and claims are absolute configurations unless otherwise specified.

Also, an "anti" configuration in the present specification and claims means that the hydroxyl group and the nitro group in 1,2-nitroalkanol compounds are in an anti configuration.

(Catalyst)

A catalyst of the present invention includes neodymium, sodium, and a ligand.

The ligand is a compound expressed by Structural Formula (1) below.

In the catalyst, the neodymium and the ligand form a complex at a molar ratio of 1:2 (neodymium:ligand).

Here, the "1:2" does not mean being strictly "1:2"; i.e., does not mean "1.0:2.0", and does mean being about "1:2". That is, the "1:2" can take a range of "1.0:1.5 to 1.0:2.4" and it is preferably a range of "1.0:1.8 to 1.0:2.2".

Structural Formula (1)

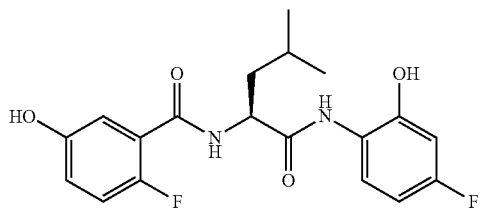

The catalyst proposed by the present inventors in JP-A No. 2010-189374 is produced using a neodymium-containing compound [Nd(O$^i$Pr)$_3$] and a sodium-containing compound [sodium bis(trimethylsilyl)amide (NaHMDS)]. In this case, neodymium and a ligand form a complex at a ratio of about 1:1.

Meanwhile, in the catalyst obtained in the below-described production method for a catalyst newly found by the present inventors, neodymium and a ligand form a complex at a molar ratio of 1:2 (neodymium:ligand). That is, the catalyst of the present invention can be stably and inexpensively prepared by the below-described production method for a catalyst.

The ratio between the neodymium and the ligand in the catalyst can be confirmed by X-ray fluorescence analysis.

Metals in the catalyst are preferably two kinds of neodymium and sodium.

The ligand in the catalyst is preferably only the compound expressed by the Structural Formula (1).

The catalyst is a heterogeneous composite metallic complex, in which the compound expressed by the Structural Formula (1) is coordinated with neodymium (Nd) and sodium (Na).

The molar ratio between neodymium and sodium in the catalyst is not particularly limited and may be appropriately selected depending on the intended purpose. However, neodymium sodium (molar ratio) is preferably 1.0:1.0 to 1.0:3.0, more preferably 1.0:1.5 to 1.0:2.5.

The molar ratio between the ligand and sodium in the catalyst is not particularly limited and may be appropriately selected depending on the intended purpose. However, the ligand sodium (molar ratio) is preferably 1.0:1.0 to 1.0:3.0, more preferably 1.0:1.5 to 1.0:2.5.

The catalyst preferably includes a carbon structure.

<Carbon Structure>

The carbon structure is not particularly limited and may be appropriately selected depending on the intended purpose so long as it is a structure formed of an unsaturated six-membered ring network of carbon. Examples thereof include carbon nanotube, carbon nanohorn, and graphene. Among them, carbon nanotube is preferable.

When the catalyst contains the carbon structure, the catalyst is easy to recover using a filter or the like. Also, even when the catalyst is recovered using a filter or the like after used for reaction, its catalytic activity will not considerably decrease. Therefore, when the carbon structure is contained in the catalyst, the catalyst is easy to recover and reuse.

The carbon nanotube may be a single-wall nanotube having a monolayer structure (SWNT) or a multi-wall nanotube having a multilayer structure (MWNT), but MWNT is preferable.

An average diameter and an average length of the carbon nanotube are not particularly limited and may be appropriately selected depending on the intended purpose.

The carbon structure may be a commercially available product. Examples of the commercially available product of the carbon nanotube include Baytubes (registered trademark) C70P and C150P (these products are of Bayer MaterialScience Co.).

An amount of the carbon structure in the catalyst is not particularly limited and may be appropriately selected depending on the intended purpose.

The catalyst is capable of synthesizing an optically active anti-1,2-nitroalkanol compound with high anti-selectivity and very high enatiomeric excess and further can be stably prepared and is inexpensive. Thus, the catalyst can be suitably used in the production of an optically active anti-1,2-nitroalkanol compound.

(Method for Producing Catalyst)

A method of the present invention for producing a catalyst includes a step of mixing a compound expressed by Structural Formula (1) below, neodymium halide, and sodium alkoxide.

The method for producing a catalyst preferably includes a step of mixing a compound expressed by Structural Formula (1) below, neodymium halide, sodium alkoxide, and a nitroethane compound.

When the catalyst contains the carbon structure, for example, the method for producing a catalyst includes a step of mixing a compound expressed by Structural Formula (1) below, neodymium halide, sodium alkoxide, a nitroethane compound, and the carbon structure.

<Compound Expressed by Structural Formula (1)>

The catalyst contains a compound expressed by Structural Formula (1) below.

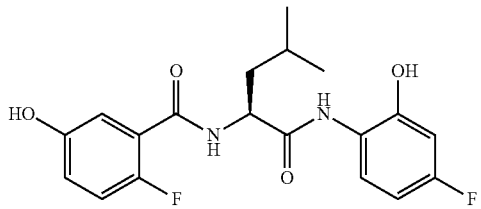

Structural Formula (1)

<Neodymium Halide>

The neodymium halide is not particularly limited and may be appropriately selected depending on the intended purpose so long as it is a halide that contains neodymium (Nd), is stable to the atmosphere, and is capable of providing neodymium to which the compound expressed by the above Structural Formula (1) will coordinate in the formation of the catalyst. Examples thereof include neodymium fluoride, neodymium chloride, and neodymium bromide.

The neodymium halide may be an anhydride or a hydrate.

Examples of the neodymium chloride include neodymium chloride hexahydrate ($NdCl_3 \cdot 6H_2O$).

The present inventors studied neodymium hydroxide, neodymium acetate, neodymium carbonate, neodymium oxide, and the like as an inexpensive and stable neodymium-containing compound other than neodymium halide. However, they are inferior to neodymium halide in terms of reproducibility.

An amount of the neodymium halide relative to the compound expressed by the Structural Formula (1) in the preparation of the catalyst is not particularly limited and may be appropriately selected depending on the intended purpose. It is preferably 0.5 mol to 2.0 mol, more preferably 0.8 mol to 1.2 mol, as an amount converted to neodymium, relative to 1 mol of the compound expressed by the Structural Formula (1).

At present, there are a few suppliers for $NdO_{1/5}(O^iPr)_{13/5}$ and its price is very expensive (30,000 yen or more per 1 g of Nd). In addition, $NdO_{1/5}(O^iPr)_{13/5}$ has low stability to the atmosphere and thus is necessary to handle in a glove box.

Meanwhile, the price of the neodymium halide is very inexpensive as compared to $NdO_{1/5}(O^iPr)_{13/5}$. For example, the price of the neodymium chloride hexahydrate ($NdCl_3 \cdot 6H_2O$) is about 100 yen per 1 g of Nd. In addition, the neodymium chloride has high stability to the atmosphere and thus is not necessary to handle in a glove box.

<Sodium Alkoxide>

The sodium alkoxide is not particularly limited and may be appropriately selected depending on the intended purpose so long as it is an alkoxide that contains sodium (Na), is stable to the atmosphere, and is capable of providing sodium to which the compound expressed by the above Structural Formula (1) will coordinate in the formation of the catalyst. Examples thereof include sodium alkoxides having 1 to 6 carbon atoms.

Examples of the sodium alkoxides having 1 to 6 carbon atoms include sodium methoxide, sodium ethoxide, sodium-n-propoxide, sodium-n-butoxide, and sodium-t-butoxide.

Among them, sodium alkoxides having 1 to 4 carbon atoms are preferable. From the viewpoints of versatility and reproducibility, sodium-t-butoxide (tBuONa) is more preferable.

An amount of the sodium alkoxide relative to the compound expressed by the Structural Formula (1) in the preparation of the catalyst is not particularly limited and may be appropriately selected depending on the intended purpose. It is preferably 1 mol to 10 mol, more preferably 3 mol to 8 mol, as an amount converted to sodium, relative to 1 mol of the compound expressed by the Structural Formula (1). Sodium bis(trimethylsilyl)amide (NaHMDS) has low stability to the atmosphere and thus is necessary to handle in a glove box.

Meanwhile, the sodium alkoxide has high stability to the atmosphere and thus is not necessary to handle in a glove box. In addition, the price of the sodium alkoxide is lower than that of sodium bis(trimethylsilyl)amide (NaHMDS).

<Nitroalkane Compound>

The nitroalkane compound is not particularly limited and may be appropriately selected depending on the intended purpose.

The nitroalkane compound may have a substituent in an alkyl group constituting its main chain. Examples of the substituent include alkoxy groups, a carboxyl group, a hydroxyl group, and halogen atoms. The substituent may be protected with a protective group. The protective group is not particularly limited and may be appropriately selected depending on the intended purpose. Reference can be made to books such as Green, et al., Protective Groups in Organic Synthesis, 3rd Edition, 1999, John Wiley & Sons, Inc.

Also, the nitroalkane compound may contain any number of double bond(s) or triple bond(s) in the alkyl chain thereof.

The nitroalkane compound is preferably a compound represented by General Formula (1) below, more preferably nitroethane.

   General Formula (1)

In the above General Formula (1), $R^1$ represents an alkyl group which has 1 to 20 carbon atoms and may have a substituent. Examples of the substituent include the above-listed substituents.

An amount of the nitroalkane compound relative to the compound expressed by the Structural Formula (1) in the preparation of the catalyst is not particularly limited and may be appropriately selected depending on the intended purpose. It is preferably 300 parts by mass to 1,000 parts by mass, more preferably 400 parts by mass to 500 parts by mass, relative to 100 parts by mass of the compound expressed by the Structural Formula (1).

<Carbon Structure>

The carbon structure is as described above.

An amount of the carbon structure relative to the compound expressed by the Structural Formula (1) in the preparation of the catalyst is not particularly limited and may be appropriately selected depending on the intended purpose. It is preferably 50 parts by mass to 400 parts by mass, more preferably 100 parts by mass to 200 parts by mass, relative to 100 parts by mass of the compound expressed by the Structural Formula (1). The amount falling within the above more preferable range is advantageous in that the resultant reaction yield will be high.

When the catalyst contains the carbon structure, a method for producing the catalyst includes, for example, a step of mixing the compound expressed by the Structural Formula (1), the neodymium halide, the sodium alkoxide, the nitroethane compound, and the carbon structure. Examples of such a method include the following methods.

—Method A—

This method is a method including: treatment A1 of mixing the compound expressed by the Structural Formula (1), the neodymium halide, the sodium alkoxide, and the carbon structure; and after the treatment A1, treatment A2 of further mixing the nitroalkane compound (hereinafter may be referred to as "Method A").

—Method B—

This method is a method including: treatment B1 of mixing the compound expressed by the Structural Formula (1), the neodymium halide, the sodium alkoxide, and the nitroalkane compound; and after the treatment B1, treatment B2 of further mixing the carbon structure (hereinafter may be referred to as "Method B").

Among them, Method A is preferable since its reaction yield is superior.

One example of the Method A will be described.

First, the compound expressed by the Structural Formula (1), the neodymium halide, and the sodium alkoxide are mixed in the presence of a solvent to obtain a white turbid suspension. Examples of the solvent include tetrahydrofuran.

Next, the carbon structure is added to the obtained suspension. Thereby, a state is established where the white turbid suspension and black precipitates (carbon structure) coexist.

Next, the nitroalkane compound is added thereto, followed by aging.

Thereby, the catalyst can be obtained.

In this method, the black catalyst, which is not white turbid, is obtained. It is believed that this is because the complex is uniformly dispersed in the carbon structure.

Next, one example of the Method B will be described.

First, the compound expressed by the Structural Formula (1), the neodymium halide, and the sodium alkoxide are mixed in the presence of a solvent to obtain a white turbid suspension. Examples of the solvent include tetrahydrofuran.

Next, the nitroalkane compound is added to the obtained suspension. Thereby, its white turbidity disappears once and then appears again.

Next, the carbon structure is added thereto, followed by aging.

Thereby, the catalyst can be obtained.

In this method, the obtained catalyst is observed to have black color, which is derived from the carbon structure, and white turbidity.

Because white turbidity is observed, it is believed that the dispersion state of the complex in the carbon structure is poorer than that in the Method A.

(Method for Producing Optically Active Anti-1,2-Nitroalkanol Compound)

A method of the present invention for producing an optically active anti-1,2-nitroalkanol compound includes allowing an aldehyde compound and a nitroalkane compound having 2 or more carbon atoms to react in the presence of the catalyst of the present invention.

<Aldehyde Compound>

The aldehyde compound is not particularly limited and may be appropriately selected depending on the intended purpose so long as it is a compound having an aldehyde group. Examples thereof include aromatic aldehyde compounds and aliphatic aldehyde compounds. The aliphatic group of the aliphatic aldehyde compound may have an aromatic ring.

The aldehyde compound may have a substituent. Examples of the substituent include alkoxy groups, a carboxyl group, a hydroxyl group, and halogen atoms. The substituent may be protected with a protective group. The protective group is not particularly limited and may be appropriately selected depending on the intended purpose. Reference can be made to books such as Green, et al., Protective Groups in Organic Synthesis, 3rd Edition, 1999, John Wiley & Sons, Inc.

Examples of the aromatic aldehyde compound include benzaldehyde, halogenobenzaldehyde, alkoxybenzaldehyde, alkylbenzaldehyde, and naphthylaldehyde.

Examples of the halogenobenzaldehyde include chlorobenzaldehyde, iodobenzaldehyde, and bromobenzaldehyde. Two or more halogen atoms may be substituted on the benzene ring thereof.

Examples of the alkoxybenzaldehyde include methoxybenzaldehyde and ethoxybenzaldehyde.

Examples of the alkylbenzaldehyde include methylbenzaldehyde and ethylbenzaldehyde.

Examples of the aliphatic aldehyde compound include alkylaldehyde and aralkylaldehyde.

Examples of the alkylaldehyde include butylaldehyde and cyclopropylaldehyde.

Examples of the aralkylaldehyde include 3-phenylpropanal, phenethylaldehyde, and benzylaldehyde.

<Nitroalkane Compound Having 2 or More Carbon Atoms>

The nitroalkane compound having 2 or more carbon atoms is not particularly limited and may be appropriately selected depending on the intended purpose.

The nitroalkane compound having 2 or more carbon atoms may have a substituent in an alkyl group constituting its main chain. Examples of the substituent include alkoxy groups, a carboxyl group, a hydroxyl group, and halogen atoms. The substituent may be protected with a protective group. The protective group is not particularly limited and may be appropriately selected depending on the intended purpose. Reference can be made to books such as Green, et al., Protective Groups in Organic Synthesis, 3rd Edition, 1999, John Wiley & Sons, Inc.

Also, the nitroalkane compound having 2 or more carbon atoms may contain any number of double bond(s) or triple bond(s) in the alkyl chain thereof.

The nitroalkane compound having 2 or more carbon atoms is preferably a compound represented by General Formula (2) below, more preferably nitroethane.

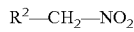    General Formula (2)

In the General Formula (2), $R^2$ represents an alkyl group which has 1 to 20 carbon atoms and may have a substituent. Examples of the substituent include the above-listed substituents.

The nitroalkane compound having 2 or more carbon atoms may be a compound identical to or different from the nitroalkane compound used in the preparation of the catalyst.

A ratio between the aldehyde compound and the nitroalkane compound having 2 or more carbon atoms in the above reaction is not particularly limited and may be appropriately selected depending on the intended purpose. An amount of the nitroalkane compound having 2 or more carbon atoms is preferably 2 mol to 20 mol, more preferably 3 mol to 10 mol, relative to 1 mol of the aldehyde compound.

An amount of the catalyst in the above reaction is not particularly limited and may be appropriately selected depending on the intended purpose. It is preferably 3 mol % to 20 mol %, more preferably 5 mol % to 10 mol %, as an amount converted to neodymium, relative to 1 mol of the aldehyde compound. The amount falling within the above more preferable range is advantageous in that the amount of the catalyst and the reaction yield will be well balanced.

A time for the reaction is not particularly limited and may be appropriately selected depending on the intended purpose. It is preferably 1 hour to 80 hours, more preferably 10 hours 70 hours.

A temperature for the reaction is not particularly limited and may be appropriately selected depending on the intended purpose. It is preferably −70° C. to −30° C., more preferably −60° C. to −40° C.

(Reaction Container, and Production Device and Production Method of Optically Active Anti-1,2-Nitroalkanol Compound)

A device of the present invention for producing an optically active anti-1,2-nitroalkanol compound includes at least a supply unit, a reaction unit, and a discharge unit; and, if necessary, further includes other units.

A method of the present invention for producing an optically active anti-1,2-nitroalkanol compound (second aspect) includes at least a supply step, a reaction step, and a discharge step; and, if necessary, further includes other steps.

A reaction container of the present invention includes at least a catalyst. The reaction container is used for the production device of the present invention and the method of the present invention for producing an optically active anti-1,2-nitroalkanol compound (second aspect).

In common fixed catalysts, catalytic active sites and carriers are covalently bound. Therefore, even if the fixed catalysts are used in a continuous reaction, the catalytic active sites are not desorbed from the carriers. Consequently, the catalytic active sites are not discharged out of reaction systems together with products. Meanwhile, unlike the common fixed catalysts, in catalysts proposed in the document (Takanori Ogawa, Naoya Kumagai, and Masakatsu Shibasaki, Angew. Chem. Int. Ed. 2013, 52, 6196-6201) and the document (Devarajulu Sureshkumar, Kazuki Hashimoto, Naoya Kumagai, and Masakatsu Shibasaki, J. Org. Chem. 2013, 78, 11494-11500) (hereinafter may be referred to as "catalysts fixed on carbon structures"), catalytic active sites and carriers (carbon structures) are not covalently bound. There are very limited examples of continuous asymmetric synthesis reactions using catalysts. Therefore, it is difficult for those skilled in art to predict that the catalysts fixed on carbon structures are able to maintain catalytic performance in the continuous asymmetric synthesis reactions. Accordingly, those skilled in art have not attempted to use the catalysts fixed on carbon structures in continuous reactions. However, the present inventors conducted extensive studies and have found that even if the catalysts fixed on carbon structures are used in continuous nitroaldol reactions, the catalytic active sites are not desorbed from the carbon structures and the catalysts fixed on carbon structures are not deteriorated in catalytic performance.

The method for producing an optically active anti-1,2-nitroalkanol compound (second aspect) may be suitably performed using the production device of an optically active anti-1,2-nitroalkanol compound. The supply step may be suitably performed using the supply unit, the reaction step may be suitably performed using the reaction unit, the discharge step may be suitably performed using the discharge unit, and the other steps may be suitably performed using the other units.

The production method. (second aspect) is a method for performing an anti-selective catalytic asymmetric nitroaldol reaction in a continuous manner in which the supply step and the discharge step are simultaneously performed.

<Supply Unit and Supply Step>

The supply unit is not particularly limited and may be appropriately selected depending on the intended purpose, so long as it is a unit configured to continuously supply an aldehyde compound and a nitroalkane compound having 2 or more carbon atoms to a reaction container. Examples thereof include a supply unit including a mixing member configured to mix the aldehyde compound with the nitroalkane compound having 2 or more carbon atoms, a first supply member configured to supply the aldehyde compound to the mixing member, a second supply member configured to supply the nitroalkane compound having 2 or more carbon atoms to the mixing member, and a connection member configured to connect the mixing member to the reaction container.

The supply step is not particularly limited and may be appropriately selected depending on the intended purpose, so long as it is a step of continuously supplying an aldehyde compound and a nitroalkane compound having 2 or more carbon atoms to a reaction container. For example, the supply step may be performed using the supply unit.

The mixing member is not particularly limited and may be appropriately selected depending on the intended purpose, so long as it is a member configured to mix the aldehyde compound with the nitroalkane compound having 2 or more carbon atoms. Examples thereof include a piping joint, a stirring mixer, an ultrasonic mixer, and a static mixer. Examples of the piping joint include a T-joint and a Y-joint.

Examples of the first supply member and the second supply member include a pump.

The first supply member may include a water removing member configured to remove water contained in the aldehyde compound. Examples of the water removing member include a desiccant. Examples of the desiccant include a molecular sieve.

The first supply member may include an impurity removing member configured to remove acidic impurities contained in the aldehyde compound. Examples of the impurity removing member include dry sodium hydrogen carbonate.

A concentration of the aldehyde compound within the first supply member (in other words, a concentration of the aldehyde compound before mixed with the nitroalkane compound having 2 or more carbon atoms in the supply step) is not particularly limited and may be appropriately selected depending on the intended purpose, but is preferably 0.01 M to 0.5 M, more preferably 0.05 M to 0.15 M from the viewpoint of adjustment to an optimum flow rate. The concentration is able to be adjusted with an organic solvent. Examples of the organic solvent include tetrahydrofuran, cyclopentyl methyl ether, diethyl ether, dichloromethane, and ethyl acetate.

A delivered volume of a liquid containing the aldehyde compound within the first supply member is not particularly limited and may be appropriately selected depending on the intended purpose, but is preferably 25 mL/h to 300 mL/h, more preferably 50 mL/h to 100 mL/h relative to 1 mmol of a catalyst to be used (on the basis of neodymium) from the viewpoint of achieving an appropriate internal pressure of a column.

A concentration of the nitroalkane compound having 2 or more carbon atoms within the second supply member (in other words, a concentration of the nitroalkane compound having 2 or more carbon atoms before mixed with the aldehyde compound in the supply step) is not particularly limited and may be appropriately selected depending on the intended purpose, but is preferably 0.1 M to 5.0 M, more preferably 0.2 M to 1.5 M from the viewpoint of rapid progress of the reaction. The concentration is able to be adjusted with an organic solvent. Examples of the organic solvent include tetrahydrofuran, cyclopentyl methyl ether, diethyl ether, dichloromethane, and ethyl acetate.

A delivered volume of a liquid containing the nitroalkane compound having 2 or more carbon atoms within the second supply member is not particularly limited and may be appropriately selected depending on the intended purpose, but is preferably 25 mL/h to 300 mL/h, more preferably 50 mL/h to 100 mL/h relative to 1 mmol of a catalyst to be used (on the basis of neodymium) from the viewpoint of achieving an appropriate internal pressure of a column.

<Reaction Unit and Reaction Step>

The reaction unit is not particularly limited and may be appropriately selected depending on the intended purpose, so long as it is a unit configured to react the aldehyde compound with the nitroalkane compound having 2 or more carbon atoms within the reaction container. For example, the reaction unit includes the reaction container and a cooling member. The cooling member is not particularly limited and may be appropriately selected depending on the intended purpose. Examples of the cooling member include a thermostat.

The reaction step is not particularly limited and may be appropriately selected depending on the intended purpose, so long as it is a step of reacting the aldehyde compound with the nitroalkane compound having 2 or more carbon atoms within the reaction container to thereby obtain an optically active anti-1,2-nitroalkanol compound. For example, the reaction step may be performed using the reaction unit.

The reaction step is preferably performed after the aldehyde compound and the nitroalkane compound having 2 or more carbon atoms are mixed together in the supply step.

<<Reaction Container>>

The reaction container contains a catalyst.

The catalyst is the catalyst of the present invention which is a catalyst obtained by mixing the compound represented by the Structural Formula (1), the neodymium halide, the sodium alkoxide, the nitroethane compound, and the carbon structure.

A material of the reaction container is not particularly limited and may be appropriately selected depending on the intended purpose. Examples thereof include stainless steel and glass.

A shape of the reaction container is not particularly limited and may be appropriately selected depending on the intended purpose. Examples thereof include cylindrical.

An internal diameter of the reaction container is not particularly limited and may be appropriately selected depending on the intended purpose, but is preferably 2 mm to 20 mm, more preferably 4 mm to 8 mm. These ranges of the internal diameter are particularly preferable ranges in the case of using 0.024 mmol (on the basis of neodymium) of a catalyst.

A length of the reaction container is not particularly limited and may be appropriately selected depending on the intended purpose, but is preferably 20 mm to 200 mm, more preferably 30 mm to 100 mm. These ranges of the length are particularly preferable ranges in the case of using 0.024 mmol (on the basis of neodymium) of a catalyst.

The reaction container includes, for example, a supply port configured to supply the aldehyde compound and the nitroalkane compound having 2 or more carbon atoms into the reaction container and a discharge port configured to discharge the optically active anti-1,2-nitroalkanol compound from the reaction container.

The discharge port preferably includes a discharge preventing member configured to prevent the catalyst from being discharged. Examples thereof include a filter.

<Discharge Unit and Discharge Step>

The discharge unit is not particularly limited and may be appropriately selected depending on the intended purpose, so long as it is a unit configured to continuously discharge the optically active anti-1,2-nitroalkanol compound, which has been obtained in the reaction unit, from the reaction container.

The discharge step is not particularly limited and may be appropriately selected depending on the intended purpose, so long as it is a step of continuously discharging the optically active anti-1,2-nitroalkanol compound from the reaction container. For example, the discharge step may be performed using the discharge unit.

The discharge is able to be performed utilizing a liquid flow in the supply unit and the supply step.

The optically active anti-1,2-nitroalkanol compound is able to be isolated by concentrating a liquid which has been discharged.

One example of the production device and the production method (second aspect) of the present invention will now be described with reference to drawings.

In such a description, continuous production of 1-(3-methoxyphenyl)-2-nitropropan-1-ol will now be described as one example of the production method (second aspect) of the present invention.

A production device of FIG. 1 includes a first pump 1, a second pump 2, a mixer 3, a connection member 4, and a catalyst column 5.

The catalyst column 5 as the reaction container is prepared as described below.

The compound represented by the Structural Formula (1), the neodymium halide, the sodium alkoxide, the nitroethane compound, and the carbon structure are mixed together to thereby obtain a catalyst. The resultant catalyst is mixed with dry Celite to thereby obtain a mixture. The resultant mixture is filled into a column to thereby obtain the catalyst column 5.

Specifically, 1-(3-methoxyphenyl)-2-nitropropan-1-ol is continuously produced as described below.

Each of dry sodium hydrogen carbonate and a dry molecular sieve is packed into a column. The first pump 1, a column containing the molecular sieve 1A, and a column containing the sodium hydrogen carbonate 1B are connected in series in this order to thereby obtain a first supply member. Thereafter, the first supply member is degassed by flushing with dry THF.

The catalyst column 5 is disposed downstream of the first supply member via a mixing member (mixer 3) and the connection member 4. Thereafter, only the catalyst column 5 is placed into a cryostat and flushed with dry THF.

Moreover, the second pump 2 as the second supply member is connected to the mixer 3.

A solution of 3-methoxybenzaldehyde in THF is delivered using the first pump 1. A solution of nitroethane in THF is delivered using the second pump 2. For example, a discharged liquid is taken from the third hour to the 24th hour and concentrated. Thus, 1-(3-methoxyphenyl)-2-nitropropan-1-ol is obtained.

According to the production device and the production method (second aspect) of the present invention, the reaction is able to be performed even if an amount of the catalyst used in the reaction is decreased to about one sixth as compared to that in a batch reaction.

According to the production device and the production method (second aspect) of the present invention, stereoselectivity in the reaction is comparable to that in the batch reaction.

Because the reaction is continuously performed in the production device and the production method (second aspect) of the present invention, the reaction container is able to be decreased in size. Consequently, a volume in which temperature needs to be controlled is decreased, resulting in easier temperature control.

According to the production device and the production method (second aspect) of the present invention, the catalyst is not contained in a liquid which has been discharged from the reaction container. Therefore, a product is able to be isolated by distilling off a solvent contained in the liquid under reduced pressure.

EXAMPLE

The present invention will now be specifically described with reference to Examples of the present invention, but is not limited thereto in any way.

Note that, in the following Examples, "THF" refers to "tetrahydrofuran," "tBuONa" refers to "sodium t-butoxide," and "MeONa" refers to "sodium methoxide."

Synthetic Example 1

<Synthesis of Compound 1>

A compound represented by Structural Formula (1) below was synthesized according to the method described in Japanese Patent Application Laid-Open (JP-A) No. 2010-189374.

Structural Formula (1)

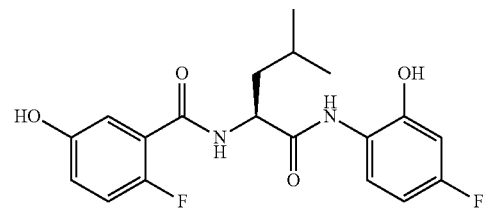

Example 1

The following reaction was performed.

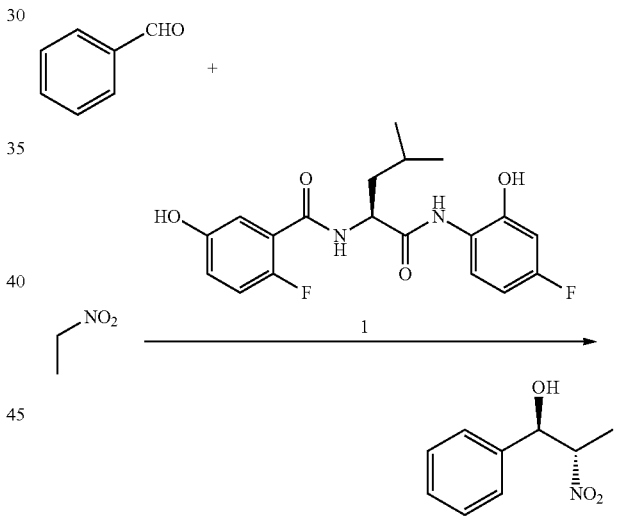

NdCl$_3$.6H$_2$O (4.3 mg, 0.012 mmol) was added to a test tube which had been dried in vacuum with heating. The inside of the system was replaced with argon. Under argon atmosphere, THF (0.10 mL) and Compound 1 synthesized in the Synthetic Example 1 (0.06 M solution in THF, 200 µL, 0.012 mmol) were added thereto and the resultant was stirred at 60° C. for 30 min. To this suspension, tBuONa (2.0 M solution in THF, 36 µL, 0.072 mmol) was added and the resultant was stirred at 60° C. for 1 hour. After cooling to room temperature, nitroethane (864, 1.2 mmol) was added thereto and the resultant was stirred for 6 hours. This suspension was transferred to an Eppendorf tube together with THF (1.2 mL) and centrifuged (10,000 rpm) for 30 seconds. The supernatant was discarded to thereby isolate a precipitate. THF (1.2 mL) was added thereto and the resultant was vigorously stirred with a vortex mixer and centrifuged (10,000 rpm) for 30 seconds again. As described above, the supernatant was discarded to thereby isolate a precipitate. THF (1.6 mL) was added thereto to thereby obtain a catalyst suspension. The thus-prepared catalyst suspension was transferred to a separately prepared test tube which had been dried in vacuum with heating. Under argon atmosphere, nitroethane (0.29 mL, 4.0 mmol) was added thereto. The test tube was transferred to a thermostat of −40° C. Benzaldehyde (41 μL, 0.40 mmol) was added to the test tube. The test tube was stirred at −40° C. for 20 hours. Then, acetic acid (0.2 M solution in THF, 0.3 mL) was added thereto and the resultant was stirred for 1 hour. At room temperature, 1 N hydrochloric acid (1 mL) was added thereto. The resultant mixed solution was extracted with ethyl acetate (1 mL), washed with saturated sodium bicarbonate water, water, and saturated saline solution, and then dried over sodium sulfate. Chemical yield: 99% ($^1$H NMR, internal standard: DMF), anti/syn: >40/1, 94% ee.

Note that, the catalyst suspension was analyzed as described below and it was confirmed that, in the catalyst, neodymium and a ligand (the compound represented by the Structural Formula (1)) formed a complex in a molar ratio of about 1:2.
<Analysis>

A catalyst sample, which had been pre-treated by a flask combustion method, was subjected to ion-chromatography to thereby quantify fluorine contained in the ligand. Moreover, a catalyst sample, which had been pre-treated by a microwave decomposition method, was subjected to ICP atomic emission spectroscopy to thereby quantify neodymium. Thus, it was confirmed that neodymium and the ligand formed a complex in the catalyst in a ratio of about 1:2 (neodymium:ligand).

Example 2

A synthesis was performed in the same manner as in Example 1, except that benzaldehyde (0.40 mmol) was changed to 2,4-dimethyl benzaldehyde (0.40 mmol) to thereby obtain a compound represented by Structural Formula below. Chemical yield: 93% ($^1$H NMR, internal standard: DMF), anti/syn: 31/1, 97% ee.

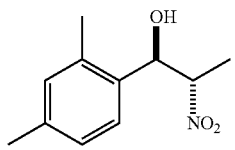

Example 3

A synthesis was performed in the same manner as in Example 1, except that benzaldehyde (0.40 mmol) was changed to 4-butoxy benzaldehyde (0.40 mmol) to thereby obtain a compound represented by Structural Formula below. Chemical yield: 88% OH NMR, internal standard: DMF), anti/syn: >40/1, 98% ee.

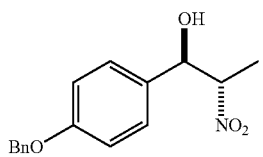 [SMILES: C[C@@H]([C@H](O)c1ccc(OCc2ccccc2)cc1)[N+](=O)[O-]]

Example 4

A synthesis was performed in the same manner as in Example 1, except that benzaldehyde (0.40 mmol) was changed to 4-methoxycarbonyl benzaldehyde (0.40 mmol) to thereby obtain a compound represented by Structural Formula below. Chemical yield: 79% OH NMR, internal standard: DMF), anti/syn: 25/1, 89% ee.

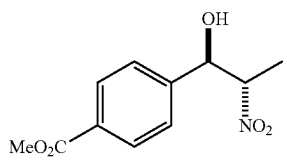

Example 5

A synthesis was performed in the same manner as in Example 1, except that tBuONa (2.0 M solution in THF, 36 μL, 0.072 mmol) was changed to MeONa (28% solution in methanol, 14 μL, 0.072 mmol) to thereby obtain a compound represented by Structural Formula below. Chemical yield: 93% (1H NMR, internal standard: DMF), anti/syn: >40/1, 94% ee.

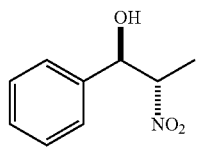

Note that, the catalyst suspension obtained in Example 5 was analyzed as described below and it was confirmed that neodymium and a ligand (the compound represented by the Structural Formula (1)) formed a complex in the catalyst in a molar ratio of about 1:2.
<Analysis>

A catalyst sample, which had been pre-treated by a flask combustion method, was subjected to ion-chromatography to thereby quantify fluorine contained in the ligand. Moreover, a catalyst sample, which had been pre-treated by a microwave decomposition method, was subjected to ICP atomic emission spectroscopy to thereby quantify neodymium. Thus, it was confirmed that neodymium and the ligand formed a complex in the catalyst in a ratio of about 1:2 (neodymium:ligand).

The chemical yield, the anti-syn ratio, and the Enantiomeric Excess (ee) in syntheses in Examples 1 to 5 were comparable to those in the case where $NdO_{1/5}(O^iPr)_{13/5}$ was used as a neodymium source and NaHMDS was used as a sodium source in the preparation of the catalyst.

Referential Example

A magnetic stirrer was added to a 20 mL evacuation test tube, which was dried in vacuum with heating. After the test tube had been left to cool, Compound 1 synthesized in Synthesis Example 1 (4.5 mg, 0.012 mmol) was added to the test tube, followed by drying in vacuum at room temperature for about 5 minutes. The test tube was purged with Ar gas, and then dry THF (0.3 mL) and $Nd_5O(O^iPr)_{13}$ (0.2 M in THF: 30 μL, 0.006 mmol, product of Kojundo Chemical Lab. Co., Ltd.) were sequentially added dropwise thereto at room temperature using a syringe. The obtained solution was cooled to 0° C., and then NaHMDS (1.0 M in THF: 12 µL, 0.012 mmol) was added dropwise thereto using a syringe. The resultant mixture was stirred at room temperature for 30 minutes to give a white suspension. The white suspension turned into a homogeneous solution by the dropwise addition of nitroethane (40 µL) at room temperature using a syringe. The homogeneous solution turned again into a white suspension when it continued to be stirred at room temperature. After stirring for 2 hours at room temperature, the white suspension was transferred to a 1.5 mL Eppendorf tube through pipetting. This tube was centrifuged at about 10,000 rpm for 5 seconds, and the supernatant was removed through decantation. Dry THF (1 mL) was added to the precipitated white catalyst remaining in the tube, and the mixture was suspended by stirring it for 30 seconds using a vortex mixer. Again, this tube was centrifuged at about 10,000 rpm for 5 seconds, and the supernatant was removed through decantation and the catalyst was washed. The catalyst after washing was added to dry THF (1 mL), followed by stirring and suspending, to thereby obtain a catalyst suspension.

Note that, the catalyst suspension was analyzed as described below and it was confirmed that neodymium and a ligand (the compound represented by the Structural Formula (1)) formed a complex in the catalyst in a molar ratio of about 1:1.

<Analysis>

A catalyst sample, which had been pre-treated by a flask combustion method, was subjected to ion-chromatography to thereby quantify fluorine contained in the ligand. Moreover, a catalyst sample, which had been pre-treated by a microwave decomposition method, was subjected to ICP atomic emission spectroscopy to thereby quantify neodymium. Thus, it was confirmed that neodymium and the ligand formed a complex in the catalyst in a ratio of about 1:1.

INDUSTRIAL APPLICABILITY

The catalyst of the present invention is capable of synthesizing an optically active anti-1,2-nitroalkanol compound with high anti-selectivity and very high enatiomeric excess and further can be stably prepared and is inexpensive, and thus it can be suitably used for a method for producing an optically active anti-1,2-nitroalkanol compound useful as a starting material of pharmaceutical products.

Aspects of the present invention are, for example, as follows.

<1> A catalyst including:
neodymium;
sodium; and
a ligand, which is a compound expressed by Structural Formula (1) below,
wherein the neodymium and the ligand form a complex at a molar ratio of 1:2 (neodymium:ligand):

Structural Formula (1)

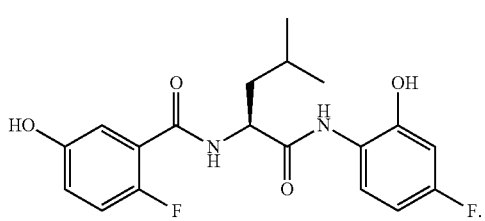

<2> A method for producing an optically active anti-1,2-nitroalkanol compound, the method including:
allowing an aldehyde compound and a nitroalkane compound having 2 or more carbon atoms to react in the presence of the catalyst according to <1>.

<3> The method for producing an optically active anti-1,2-nitroalkanol compound according to <2>, wherein the nitroalkane compound having 2 or more carbon atoms is nitroethane.

<4> A method for producing a catalyst, the method including:
mixing a compound expressed by Structural Formula (1) below, neodymium halide, and sodium alkoxide:

Structural Formula (1)

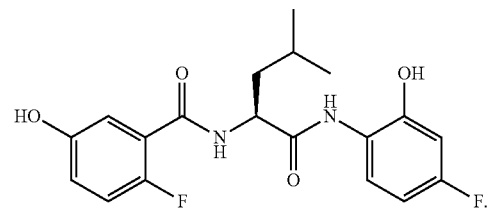

<5> The method for producing a catalyst according to <4>, wherein the neodymium halide is neodymium chloride.

<6> The method for producing a catalyst according to <4> or <5>, wherein the sodium alkoxide is sodium alkoxide having 1 to 6 carbon atoms.

<7> The method for producing a catalyst according to any one of <4> to <6>, wherein a nitroalkane compound is further mixed.

REFERENCE SIGNS LIST 1 first pump
1A column
1B column
2 second pump
3 mixer
4 connection member
5 catalyst column

The invention claimed is:

1. A catalyst comprising:
neodymium;
sodium; and
a ligand, which is a compound expressed by Structural Formula (1) below,
wherein the neodymium and the ligand form a complex at a molar ratio of 1:2 (neodymium:ligand):

Structural Formula (1)

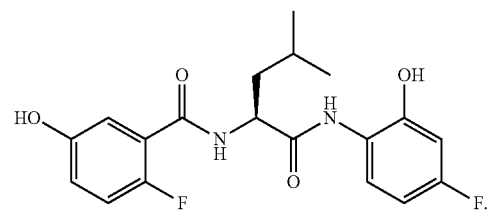

2. A method for producing an optically active anti-1,2-nitroalkanol compound, the method comprising:

allowing an aldehyde compound and a nitroalkane compound having 2 or more carbon atoms to react in the presence of the catalyst according to claim 1.

3. The method for producing an optically active anti-1,2-nitroalkanol compound according to claim 2, wherein the nitroalkane compound having 2 or more carbon atoms is nitroethane.

4. A method for producing a catalyst, the method comprising:

mixing a compound expressed by Structural Formula (1) below, neodymium halide, and sodium alkoxide Structural Formula (1)

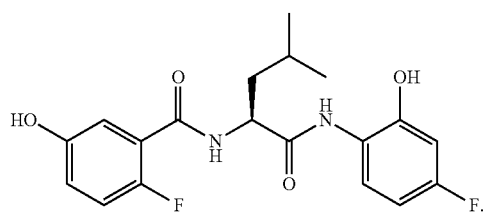

5. The method for producing a catalyst according to claim 4, wherein the neodymium halide is neodymium chloride.

6. The method for producing a catalyst according to claim 4, wherein the sodium alkoxide is sodium alkoxide having 1 to 6 carbon atoms.

7. The method for producing a catalyst according to claim 4, wherein a nitroalkane compound is further mixed.

8. The catalyst according to claim 1, wherein the catalyst does not comprise a carbon structure.

9. The method for producing an optically active anti-1,2-nitroalkanol compound according to claim 2, wherein the catalyst does not comprise a carbon structure.

10. The method for producing a catalyst according to claim 4, wherein the catalyst does not comprise a carbon structure.

* * * * *